(12) United States Patent
Shirahata

(10) Patent No.: US 8,447,082 B2
(45) Date of Patent: May 21, 2013

(54) MEDICAL IMAGE DISPLAYING APPARATUS, MEDICAL IMAGE DISPLAYING METHOD, AND MEDICAL IMAGE DISPLAYING PROGRAM

(75) Inventor: Takashi Shirahata, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 707 days.

(21) Appl. No.: 12/599,312

(22) PCT Filed: Jun. 3, 2008

(86) PCT No.: PCT/JP2008/060179
§ 371 (c)(1),
(2), (4) Date: Nov. 9, 2009

(87) PCT Pub. No.: WO2008/152938
PCT Pub. Date: Dec. 18, 2008

(65) Prior Publication Data
US 2010/0215228 A1    Aug. 26, 2010

(30) Foreign Application Priority Data
Jun. 11, 2007 (JP) ................ 2007-153540

(51) Int. Cl.
*G06K 9/00* (2006.01)

(52) U.S. Cl.
USPC ........................................... 382/128

(58) Field of Classification Search
USPC ............... 382/128; 600/439, 473, 475–476
See application file for complete search history.

(56) References Cited

U.S. PATENT DOCUMENTS 7,369,691 B2 * 5/2008 Kondo et al. ................ 382/128
7,376,456 B2 * 5/2008 Marshik-Geurts et al. ... 600/473
2001/0007408 A1 * 7/2001 Furusawa et al. ............ 313/407
2006/0098851 A1 * 5/2006 Shoham et al. ............... 382/128
2006/0280347 A1   12/2006 Shirahata et al.
2008/0255449 A1 * 10/2008 Warnking et al. ............ 600/439
2011/0255754 A1 * 10/2011 Dmitrieva et al. ............ 382/128

FOREIGN PATENT DOCUMENTS

| JP | 11-99142 | 4/1999 |
| JP | 2003-265408 | 9/2003 |
| JP | 2004-141612 | 5/2004 |
| JP | WO2005/011501 A1 | 2/2005 |

OTHER PUBLICATIONS

Dec. 16, 2011 European search report in connection with counterpart European patent application No. 08 76 4992.

(Continued)

*Primary Examiner* — Gerald J. O'Connor
*Assistant Examiner* — Edward Winston, III
(74) *Attorney, Agent, or Firm* — Cooper & Dunham LLP

(57) ABSTRACT

A medical image display apparatus in accordance with the present invention includes a means (13) for selectively inputting a desired medical image from among medical images taken by a medial-image radiography system, a deployed image creating means (11a) for reading the selectively inputted medical image from the medical-image radiography system or an external storage device, and producing a deployed image of a region of a luminal organ contained in the read medical image, and a control means (11) for controlling display of the created deployed image on a display means (18). The control means (11) includes a correcting means (11b) for calculating a magnitude of a variance between radial information, which contracts or expands to a predetermined value in the region of the luminal organ, and radial information on a nearby position, and correcting a distortion of the deployed image, which is created by the deployed image creating means (11a), on the basis of the calculated magnitude of the variance between the pieces of radial information.

11 Claims, 10 Drawing Sheets

OTHER PUBLICATIONS

Oda, Masahiro, et al. (2005), "Development of a Navigation-Based CAD System for Colon," MICCAI 2005, LNCS 3749, pp. 696-703.

Oda, Masahiro, et al., "Evaluation of Distortion Reduction Method for Virtual Unfolded Views of the Colon," *Medical Imaging Technology*, vol. 24, No. 5, pp. 419-428, 2006 (English translation of Abstract).

* cited by examiner

FIG. 6
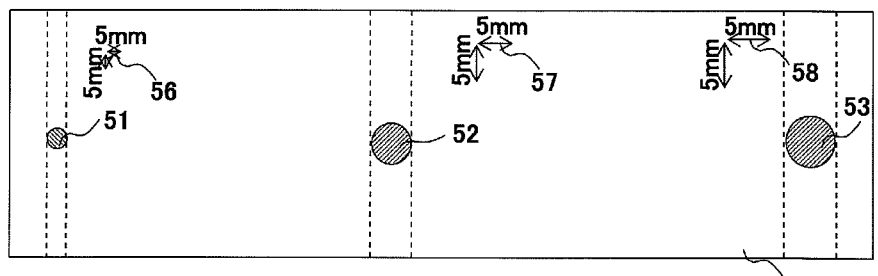
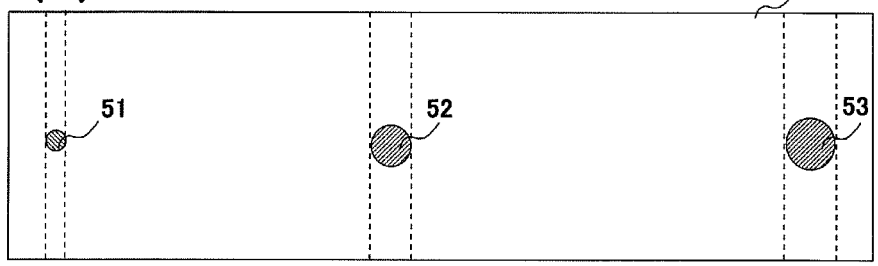
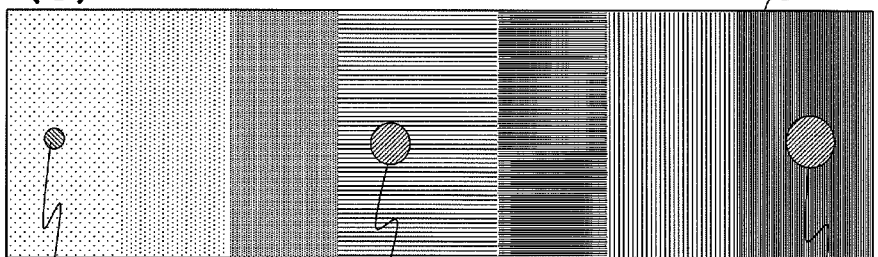

MEDICAL IMAGE DISPLAYING APPARATUS, MEDICAL IMAGE DISPLAYING METHOD, AND MEDICAL IMAGE DISPLAYING PROGRAM

TECHNICAL FIELD

The present invention relates to a deployed image display technology for evolving and displaying an internal wall portion of a desired luminal organ in a medical image obtained from a medical image diagnosis system. The present invention relates to a medical image display apparatus, a medial image display method, and a medical image display program making it possible to observe the size of a lesion, which exists in the internal wall portion, with a geometric distortion minimized.

BACKGROUND ART

In non-patent document 1, a deployed image display technology for evolving the length in a circumferential direction of a luminal organ into a length proportional to the radius of the luminal organ is disclosed.

The non-patent document 1 refers to Int. J. CARS. (vol. 1, pp. 373-375, 2006) written by M. Oda et al.

DISCLOSURE OF THE INVENTION

Problem to be Solved by the Invention

However, the foregoing disclosed technology is limited to creation of a deployed image proportional to the radius of the luminal organ, and is confronted with an unsolved issue of geometrically precisely displaying a lesion such as a polyp.

An object of the present invention is to provide a medical image display apparatus, a medical image display method, and a medical image display program capable of geometrically precisely calculating morphological information on a lesion.

Means for Solving the Problem

A medical image display apparatus in accordance with the present invention includes a means for selectively inputting a desired medical image from among medical images taken by a medical-image radiography system, a deployed image creating means for reading the selectively inputted medical image from the medical-image radiography system or an external storage device, and producing a deployed image of a region of a luminal organ contained in the read medical image, and a control means for controlling display of the created deployed image on a display means. Herein, the control means includes a correcting means for calculating a magnitude of a variance between radial information, which contracts or expands to a predetermined value in the region of the luminal organ, and radial information on a nearby position, and correcting a distortion in the deployed image, which is created by the deployed image creating means, on the basis of the calculated magnitude of the variance between the pieces of radial information.

A medical image display method in accordance with the present invention includes a step of selectively inputting a desired medical image from among medical images taken by a medical-image radiography system, a step of reading the selectively inputted medical image from the medical-image radiography system or an external storage device, and producing a deployed image of a region of a luminal organ contained in the read medical image, a step of calculating a magnitude of a variance between radial information, which contracts or expands to a predetermined value in the region of the luminal organ, and radial information on a nearby position, and correcting a distortion in the deployed image, which is created by the deployed image creating means, on the basis of the calculated magnitude of the variance between the pieces of radial information, and a step of controlling display of the corrected deployed image on a display means.

A medical image display program in accordance with the present invention causes a computer to exert the features of a step of selectively inputting a desired medical image from among medical images taken by a medical-image radiography system, a step of reading the selectively inputted medical image from the medical-image radiography system or an external storage device, and producing a deployed image of a region of a luminal organ contained in the read medical image, a step of calculating a magnitude of a variance between radial information, which contracts or expands to a predetermined value in the region of the luminal organ, and radial information on a nearby position, and correcting a distortion in the deployed image, which is created by the deployed image creating means, on the basis of the calculated magnitude of the variance between the pieces of radial information, and a step of controlling display of the corrected deployed image on a display means.

Advantage of the Invention

According to the present invention, a medical image display apparatus, a medical image display method, and a medical image display program capable of geometrically precisely calculating morphological information on a lesion can be provided.

BRIEF DESCRIPTION OF THE DRAWINGS

FIG. 6 It shows examples of display images in the second, third, and fourth embodiments different from that shown in FIG. 5;

DESCRIPTION OF REFERENCE NUMERALS

Figure 1:
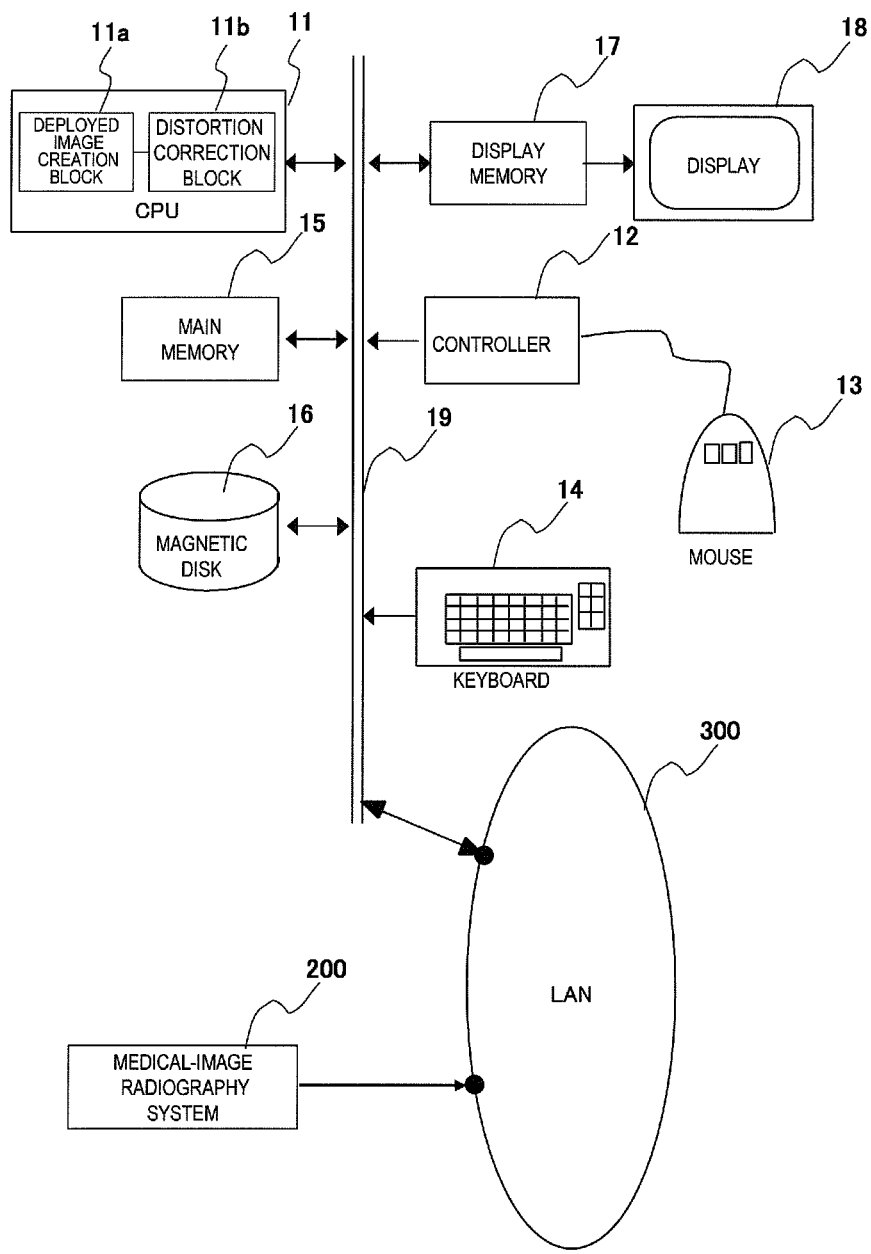
FIG. 1 It is a block diagram showing an example of the configuration of a medical image display apparatus in accordance with the present invention.

11: CPU, 11a: central line-of-luminal organ extraction block, 11b: deployed image-of-luminal organ creation block, 12: controller, 13: mouse, 14: keyboard, 15: main memory, 16: magnetic disk, 17: display memory, 18: display, 200: medical-tomographic image radiography system, 300: local area network (LAN).

Best Mode for Carrying Out the Invention

The best mode for carrying out the present invention will be described below in conjunction with the appended drawings. In all the drawings for use in explaining the embodiments of the present invention, the same reference numerals are assigned to components having identical capabilities. An iterative description will be omitted.

FIG. 1 is a block diagram showing an example of the configuration of a medical image display apparatus in accordance with the present invention. The medical image display apparatus has a controller 12, a keyboard 14, a main memory 15, a magnetic disk 16, and a display memory 17 connected to a CPU 11 over a data transfer bus 19 so that signal transmission or reception can be achieved. The CPU 11 is connected to a medical-image radiography system 200 over the data transfer bus 19 and a local area network (LAN) 300 so that signal transmission or reception can be achieved. A mouse 13 is connected to the controller 12 and a display 18 is connected to the display memory 17 so that signal transmission or reception can be achieved. Herein, when it says that signal transmission or reception can be achieved, it signifies a state in which signal transmission or reception can be achieved mutually or from one component to another electrically or optically irrespective of by wire or by radio.

The CPU 11 runs computer programs to control the components connected thereto. Concrete examples of the computer programs extract a luminal organ contained in medical image data, obtain the central line of the extracted luminal organ through calculation, cut the luminal organ in the longitudinal direction thereof so as to create a deployed image (capability of a deployed image creation block 11a), or correct a distortion of the created deployed image (capability of a distortion correction block 11b). The controller 12 transmits various kinds of data items including data of a magnitude of a shift of a position, which is obtained by a sensor included in the mouse 13, and input data inputted with a button switch included in the mouse 13, to the CPU 11 over the data transfer bus 19. When an operator moves a cursor of the mouse 13 to an image displayed on the display 18, or a switch produced by a software such as a radio switch, the operator clicks the mouse 13 at the cursor moved position. Eventually predetermined input data is inputted.

The keyboard 14 is an input device to be used mainly for a case where character entry is preferable, such as, for entry of ID information that specifies a medical image which should be read from the magnetic disk 16 or for entry of a diagnostic report concerning a medical image displayed on the display 18. The main memory 15 is used as a work area for any of the computer programs to load any of various computer programs from the magnetic disk 16, or in which medical image data or an intermediate progress of computation is stored during the computation by any of the computer programs. The magnetic disk 16 is a generic term representative of external storage devices in a computer system. Part of the capability is to receive a medical tomographic image, which is taken by the medical-image radiography system 200, over a network such as the LAN 300, and store it.

The external storage devices include various storage media such as a flexible disk, an optical (magnetic) disk, a ZIP memory, and a USB memory. Before data to be displayed on the screen out of the results of computation by the CPU 11 is transferred to the display 18 in the form of a signal, the data is temporarily stored in the display memory 17. The medical image transferred from the display memory 17 in the form of a signal and various pieces of appended information are stored in the display 18.

Over the data transfer bus 19, according to a program to be run by the CPU 11, data transfer is performed between components connected over the data transfer bus 19. The medical-image radiography system 200 refers to a system capable of obtaining a tomographic image of a subject, such as, an X-ray CT system, an MRI system, an ultrasound system, a scintillation camera system, a PET system, or a SPECT system. The LAN 300 is a network over which the medical-image radiography system 200 and medical image display apparatus are connected to each other so that signal transmission or reception can be achieved. The LAN may be the Internet or any other public network.

Next, the first to sixth embodiments will be described below.

[First Embodiment]

Figure 2:
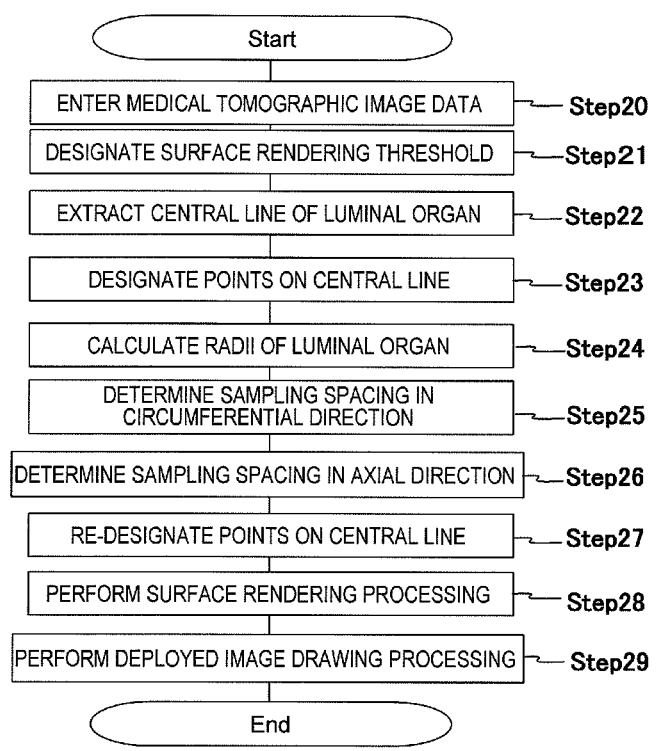
FIG. 2 It is a flowchart for explaining a processing procedure of the first embodiment of the medical image display apparatus shown in FIG. 1.
Figure 3:
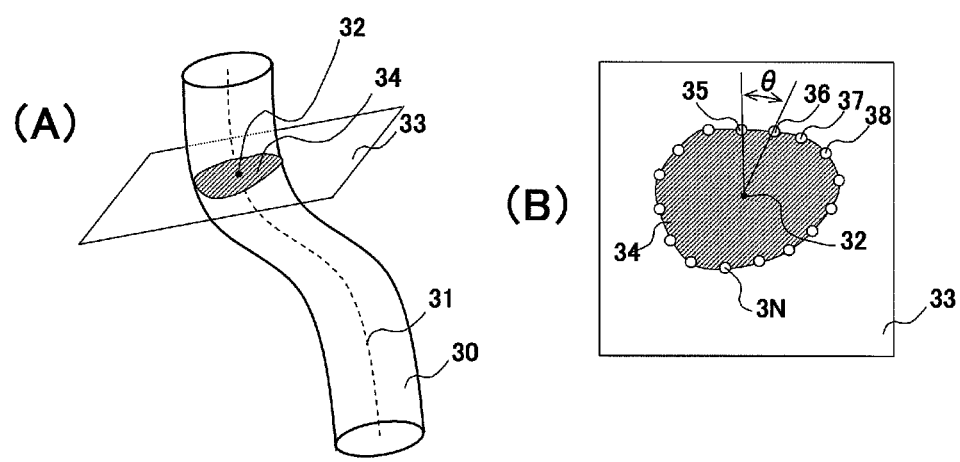
FIG. 3 It includes explanatory diagrams of step 24 in the first embodiment.
Figure 4:
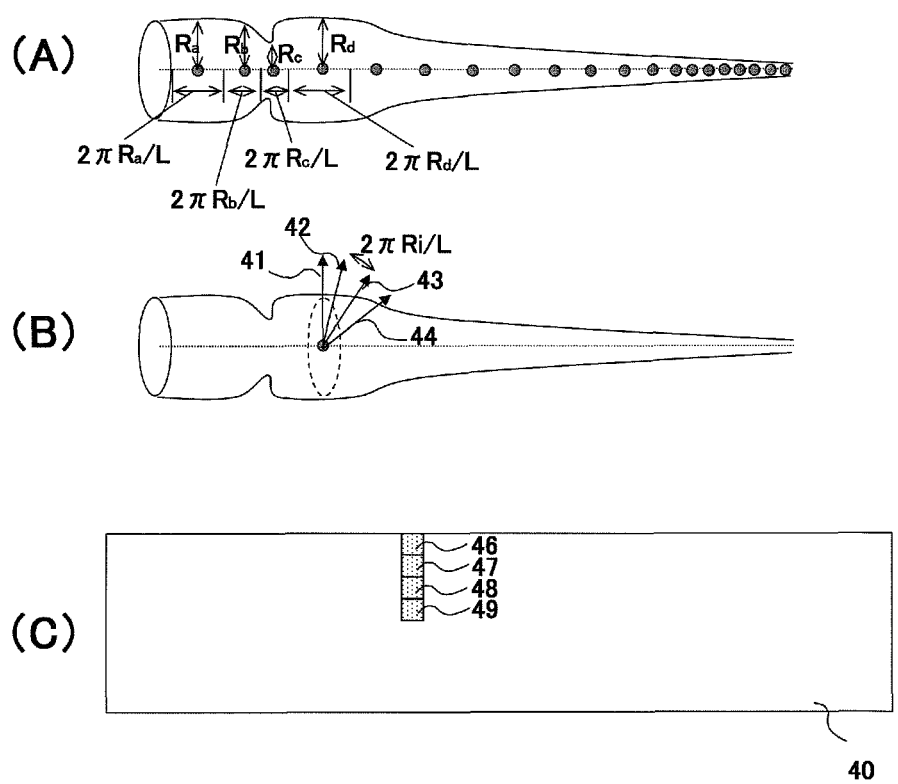
FIG. 4 It includes explanatory diagrams of steps 27 and 28 in the first embodiment.
Figure 5:
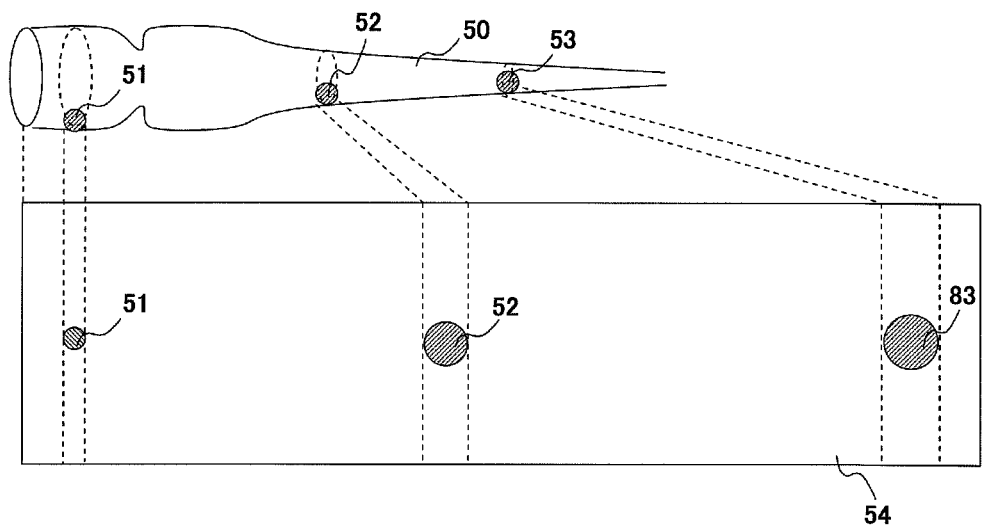
FIG. 5 It shows an example of a display image of the first embodiment resulting from FIG. 2.

The first embodiment of the present invention will be described using FIG. 2 to FIG. 5, and the procedure of a program will be described in conjunction with the flowchart of FIG. 2. FIG. 2 is a flowchart for explaining a processing procedure of the first embodiment of the medical image display apparatus shown in FIG. 1. FIG. 3 is an explanatory diagram of step 24 of the first embodiment. FIG. 4 includes explanatory diagrams of steps 27 and 28 of the first embodiment. FIG. 5 shows an example of a display image of the first embodiment resulting from FIG. 2.

An operator uses the mouse 13 or keyboard 14 to designate and enter a group of medical tomographic images that represents an object of observation. Herein, the object of observation shall be an intestinal region of the small intestine or large intestine. The CPU 11 sets data of the group of medical tomographic images, which results from radiography of the intestinal region that is the object of observation, from the magnetic disk 16 or medical-image radiography system 200 into the main memory 15 (step 20).

The operator uses the mouse 13 or keyboard 14 to designate and enter various parameters that are needed to perform rendering processing and that include a threshold for use in surface rendering during deployed image creation (step 21).

The CPU 11 uses a known central line-of-luminal organ extracting method to extract a central line of a region of a luminal organ, which is an object of observation, from the entered medical tomographic image. As for the known central line-of-luminal organ extracting method, a technology described in, for example, JP-A-2006-42969 is adopted (step 22).

The CPU 11 designates sample points on the central line of the luminal organ extracted at step 22 at intervals of an arbitrary spacing. Herein, the arbitrary spacing may be one pixel, or any other predesignated value may be adopted (step 23).

The CPU 11 obtains the radius of the luminal organ within a section that is orthogonal to the central line at each of the points on the central line designated at step 23. The way of obtaining the radius will be described in conjunction with FIG. 3. To begin with, a central line 31 of a luminal organ 30 shall be obtained as shown in FIG. 3. Now, a discussion will be made of a case where the radius of a luminal region 34 on a section 33 orthogonal to the central line at a point 32 on the central line is obtained. Points 35 to 3N are designated on the perimeter of the luminal organ so that an angle θ measured with the point 32 on the central line as an apex will remain constant. The radius of the luminal organ may be a mean value of distances from the point 32 on the central line to the respective points 35 to 3N. Another calculation method for the radius of the luminal organ is to approximate the points 35 to 3N to a circle and adopt the radius of the circle.

The CPU 11 obtains the radius of the luminal organ at each of points i on the central line in the same manner. Thus, the radii of the luminal organ obtained at the points i on the central line shall be the radii Ri (step 24).

The CPU 11 obtains a sampling pitch in the circumferential direction of a deployed image. The sampling pitch is varied depending on the value of the radius of the luminal organ obtained at step 24, and expressed as $2\pi Ri/L$. Herein, L denotes the predesignated pixel count in the circumferential direction of the deployed image. Otherwise, an operator may arbitrarily designate L using an input device such as the mouse 13 or keyboard 14 through a GUI (step 25).

The CPU 11 obtains a sampling pitch in the axial direction (direction substantially along the central line) of the deployed image. The sampling pitch is varied depending on the value of the radius of the luminal organ obtained at step 74. The sampling pitch is, similarly to the one in the circumferential direction, expressed as $2\pi Ri/L$ (step 26).

The CPU 11 re-designates points on the central line according to the sampling pitch in the axial direction obtained at step 26. As shown in FIG. 4(A), points are re-designated on the central line so that the sampling pitch will be $2\pi Ri/L$ with a point i as a center. Through the re-designation, distortion correction is completed before a deployed image is produced (step 27).

The CPU 11 traces, as shown in FIG. 4(B), rays (including rays 41 to 44) on a section, which is orthogonal to the central line from each of the points on the central line re-designated at step 27 (in short, according to a ray tracing method), so as to achieve rendering processing. At this time, the distance between adjoining rays shall be equal to the sampling pitch $2\pi Ri/L$ in the circumferential direction obtained at step 25. As the rendering method, a surface rendering method shall be adopted in this case. The CPU 11 stores in the main memory 15 the values, which are obtained according to the surface rendering method, as associated pixels of a deployed image 40 as shown in FIG. 4(C). More particularly, the values obtained from the rays 41 to 44 are equivalent to pixels 46 to 49. The CPU 11 performs the same processing on all the points designated on the central line so as to obtain a deployed image. The pixel count in the circumferential direction of the deployed image is a predesignated value L, and the pixel count in the axial direction thereof is equal to the number of points designated on the central line (step 28).

The CPU 11 sets data of the deployed image, which is created at step 28, in the display memory 17. The deployed image whose data is set in the display memory 17 is displayed on the display 18. In another image display area on the display 18 on which the deployed image is displayed, an MPR image of an arbitrary position, a virtual endoscopic image, a 3D image, or an axial, sagittal, or coronal image may be displayed. On the display 18, the deployed image may be displayed in two or three rows (step 29).

As mentioned above, a medical image display apparatus and program capable of geometrically precisely calculating morphological information on a lesion can be provided. An advantage inherent to the first embodiment is such that since a resolution in a circumferential direction and a resolution in an axial direction are identical to each other, a deployed image with little distortion can be provided.

[Second Embodiment]

FIG. 6(A) shows an example of a display image of the second embodiment resulting from FIG. 2. Herein, the CPU 11 produces pieces of dimensional information on 5 mm in a longitudinal direction and a lateral direction of a deployed image on the basis of a slice thickness of a CT image or a slice pitch. In the drawing, the dimension is expressed with arrows in the longitudinal direction and lateral direction of the deployed image. Any form may be adopted as long as the dimension is indicated in the form. Further, the CPU 11 sets data in the display memory 17 so that the pieces of produced dimensional information and the deployed image of the first embodiment can be displayed on the display 18 while being superposed on each other. On the display 18, an image in which the pieces of produced dimensional information and the deployed image of the first embodiment are superposed on each other is displayed. According to the present embodiment, a medical image display apparatus and program capable of geometrically precisely calculating morphological information on a lesion can be provided. An advantage inherent to the second embodiment is such that information on the size of a diseased site in a deployed image can be intuitively provided for a diagnostician.

[Third Embodiment]

FIG. 6(B) shows an example of a display image of the third embodiment resulting from FIG. 2. Herein, the CPU 11 produces a scale, which indicates a dimension that varies depending on a position in the longitudinal direction of a deployed image, on the basis of a slice thickness of a CT image or a slice pitch. In the drawing, the dimension is expressed with a scale 5A below the longitudinal direction of the deployed image. Any form may be adopted as long as the dimensional information can be expressed in the form. Further, the CPU 11 sets data in the display memory 17 so that the produced scale will be located below the deployed image of the first embodiment. On the display 18, an image in which the produced scale and the deployed image of the first embodiment are juxtaposed is displayed. According to the present embodiment, a medical image display apparatus and program capable of geometrically precisely calculating morphological information on a lesion can be provided. An advantage inherent to the third embodiment is such that a diseased site is easily seen because the scale is not superposed on a deployed image, and broad dimensional information on the diseased site can be provided.

[Fourth Embodiment]

FIG. 6(C) shows an example of a display image of the fourth embodiment resulting from FIG. 2. Herein, the CPU 11 produces color differentiation information according to a color pallet 5b in consideration of a dimension, which varies depending on a position in the longitudinal direction of a deployed image, on the basis of a slice thickness of a CT image or a slice pitch. Further, the CPU 11 appends colors, which are represented by the produced color differentiation information, to the deployed image of the first embodiment, and sets data of the colored deployed image in the display memory 17. On the display 18, the colored deployed image is displayed. According to the present embodiment, a medical image display apparatus and program capable of geometrically precisely calculating morphological information on a lesion can be provided. An advantage inherent to the fourth embodiment is such that since a condition of occlusion or the like shown in a deployed image is displayed as a color distribution image, the graveness of a diseased site is easily seen.

[Fifth Embodiment]

Figure 7:
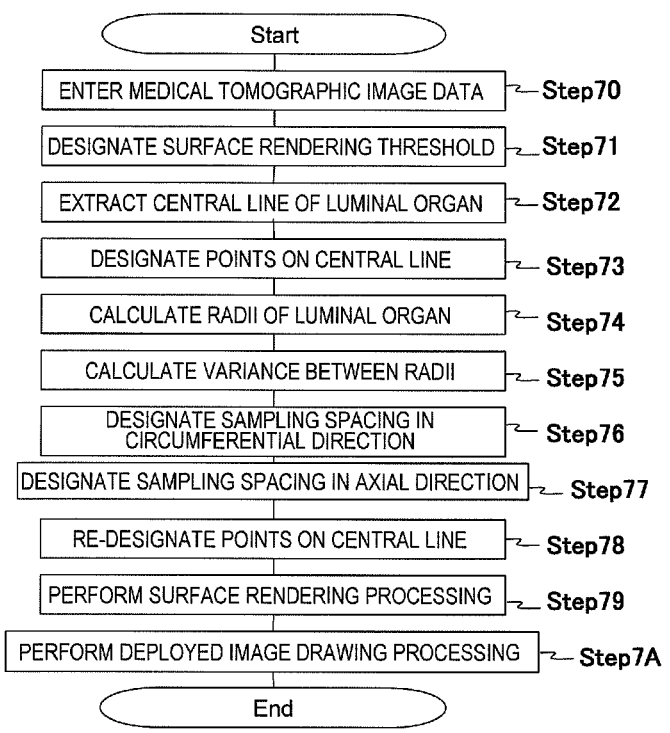
FIG. 7 It is a flowchart for explaining a processing procedure of the fifth embodiment of the medical image display apparatus shown in FIG. 1.
Figure 8:
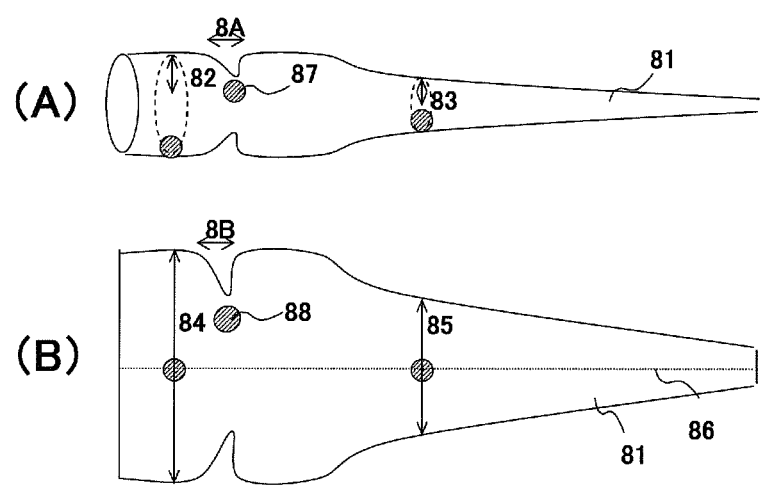
FIG. 8 It shows examples of display images of the fifth embodiment resulting from FIG. 7.

The fifth embodiment of the present invention will be described below. FIG. 7 is a flowchart for explaining a processing procedure of the fifth embodiment of the medical image display apparatus shown in FIG. 1. FIG. 8 shows examples of display images of the fifth embodiment resulting from FIG. 7. In the first embodiment, the length in the circumferential direction of a deployed image remains constant. In the fifth embodiment, the length in the circumferential direction is varied depending on the radius of a luminal organ. In this case, the sampling pitch in the circumferential direction and that in the axial direction are set to the same constant value (unit length or the like). However, for a region in which a variance in the radius is abrupt, the sampling pitch is varied according to $2\pi RiA/L$ in order to alleviate a distortion of a deployed image. FIG. 7 is a flowchart for explaining processing of the fifth embodiment. A description will be made of steps. A description of steps 70 to 74 (identical to steps 20 to 24) at which the same pieces of processing as those in the first embodiment are performed will be omitted.

The CPU 11 obtains a ratio $r=Ri/Ri-1$ of adjoining ones of the radii of a luminal organ at points on the central line obtained at step 74 (24) (step 75).

The CPU 11 obtains the sampling pitch in the circumferential direction of the deployed image. If the radio r of adjoining radii obtained at step 75 has a relationship of $r0<r<r1$ to predesignated thresholds r0 and r1, a predesignated constant value (unit length or the like) is adopted as the sampling pitch in the circumferential direction. If the relationship is $r<r0$ or $r>r1$, that is, if a variance between radii is abrupt, $2\pi RiA/L$ is adopted as the sampling pitch in the same manner as it is in the first embodiment (step 76).

The CPU 11 obtains the sampling pitch in the axial direction of a deployed image. The sampling pitch in the axial direction is identical to the sampling pitch in the circumferential direction obtained at step 76 (step 77).

The CPU 11 re-designates points on the central line according to the sampling pitch in the axial direction obtained at step 77 (step 78).

The CPU 11 performs, similarly to rendering processing performed in the first embodiment, rendering processing by tracing rays from the points on the central line designated at step 78. Obtained pixel values are assigned to associated pixels in the deployed image (step 79).

The CPU 11 sets data of the deployed image, which is created at step 79, in the display memory 17. The deployed image whose data is set in the display memory 17 is displayed on the display 18 (step 7A).

According to the present embodiment, a medical image display apparatus and program capable of geometrically precisely calculating morphological information on a lesion can be provided. An advantage inherent to the fifth embodiment is that a deployed image which has a distortion thereof alleviated and on which the lengths of the radii of a luminal organ are reflected can be obtained.

[Sixth Embodiment]

Figure 9:
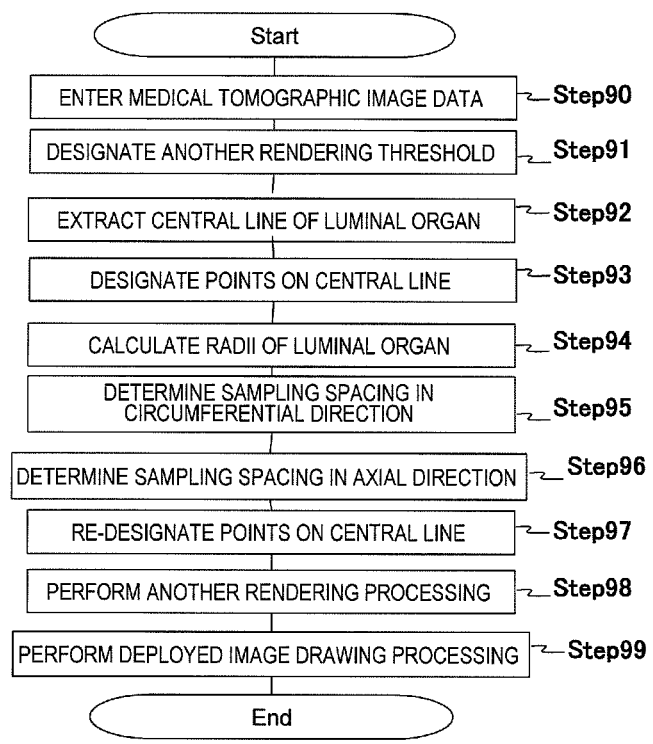
FIG. 9 It is a flowchart for explaining a processing procedure of the sixth embodiment of the medical image display apparatus shown in FIG. 1.
Figure 10:
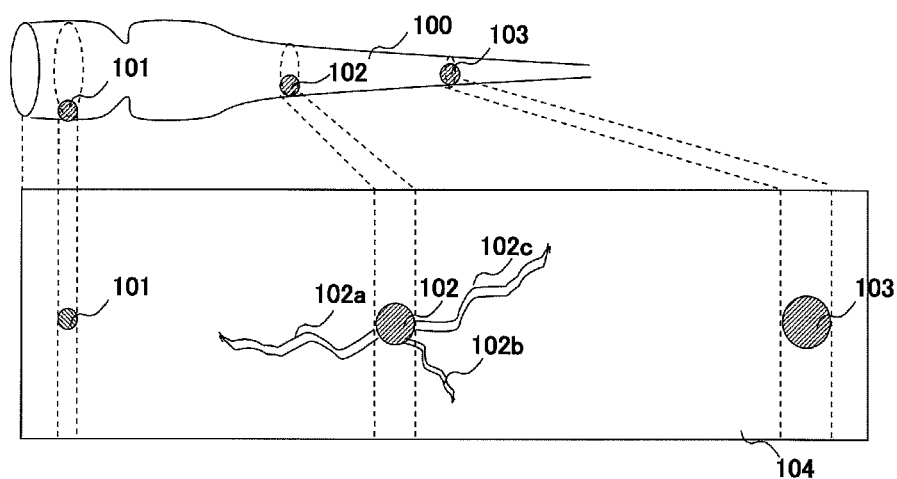
FIG. 10 It shows an example of a display image of the sixth embodiment resulting from FIG. 9.

The sixth embodiment of the present invention will be described below. FIG. 9 is a flowchart for explaining a processing procedure of the sixth embodiment of the medical image display apparatus shown in FIG. 1. FIG. 10 shows an example of a display image of the sixth embodiment resulting from FIG. 9. In the first embodiment, the surface rendering method is adopted as a rendering method for a deployed image. In the sixth embodiment, a description will be made of a case where a rendering method other than the surface rendering method is adopted. As the other rendering methods, a maximum intensity projection (MIP) method, a minimum intensity projection (MinP) method, a ray sum method, and a volume rendering method are known. Herein, the MIP method is taken. FIG. 9 shows a processing flow of the sixth embodiment. Steps will be described below. A description of steps 90 and 92 to 97 (identical to steps 20 and 22 to 27) at which pieces of processing identical to those of the first embodiment are performed is omitted.

An operator designates a threshold or the like employed in the MIP method for creating a deployed image (step 91).

The CPU 11 traces rays (including rays 101 to 104) on each of sections orthogonal to a central line from the points on the central line designated at step 97 (27), projects a maximum value out of the rays (rendering processing according to the MIP method), and thus produces a deployed image. At this time, an angle between adjoining rays should be equal to the sampling pitch $2\pi Ri/L$ in the circumferential direction obtained at step 95 (25) (step 98).

The CPU 11 sets data of the deployed image created at step 79 in the display memory 17. The deployed image whose data is set in the display memory 17 is displayed on the display 18 (step 99).

Eventually, a deployed image of a luminal organ to which pieces of ambient information on an organ including pieces of information on feeding vessels, which feed nutrition to a tumor, such as pieces of information 102a, 102b, and 102c shown in FIG. 10 and information on invasion of the tumor are added is obtained.

According to the present embodiment, a medical image display apparatus and program capable of geometrically precisely calculating morphological information on a lesion can be provided. An advantage inherent to the sixth embodiment is such that when a deployed image is locally viewed, since the sampling pitch in the circumferential direction and that in the axial direction are identical to each other, a spherical region is rendered as a nearly spherical shape, and missing a lesion due to a distortion or the like is minimized.

Referring to the appended drawings, the preferred embodiments of the medical image display apparatus in accordance with the present invention have been described so far. However, the present invention will not be limited to the embodiments. It is apparent that a person with ordinary skill in the art will think of various examples of modifications or corrections within the scope of the technological idea disclosed in this application. The examples shall belong to the technological scope of the present invention.

The invention claimed is:

1. A medical image display apparatus comprises:
    a means for selectively inputting a desired medical image from among medical images taken by a medical-image radiography system;
    a deployed image creating means for reading the selectively inputted medical image from the medical-image radiography system or an external storage device, and producing a deployed image of a region of a luminal organ contained in the read medical image; and
    a control means for controlling display of the created deployed image on a display means, wherein the control means includes a correcting means for calculating a magnitude of a variance between radial information, which contracts or expands to a predetermined value in the region of the luminal organ, and radial information on a nearby position, and correcting a distortion of the deployed image, which is created by the deployed image creating means, on the basis of the calculated magnitude of the variance between the pieces of radial information, and wherein the correcting means obtains a sampling pitch in the circumferential direction of the deployed image on the basis of the radical information and makes a sampling pitch in the axial direction of the deployed image the same as the sampling pitch in the circumferential direction.

2. The medical image display apparatus according to claim 1, characterized in that the correcting means obtains a central line of the region of the luminal organ, extends segments radially from the obtained central line, and calculates a mean value of distances, by which the segments extend to reach the perimeter of the region of the luminal organ, as radial information on the region of the luminal organ.

3. The medical image display apparatus according to claim 1, characterized in that the correcting means obtains a central line of the region of the luminal organ, extends segments radially from the obtained central line, approximates a polygon, which links points on the perimeter of the region of the luminal organ to which the segments reach, to a circle, and adopts a radius of the approximate circle as radial information on the region of the luminal organ.

4. The medical image display apparatus according to claim 1, characterized in that the control unit includes a means for producing local dimensional information on the region of the luminal organ on the basis of the magnitude of the variance between the pieces of radial information calculated by the correcting means, and implements control so that the produced dimensional information and deployed image will be displayed on the display means while being superposed on each other.

5. The medical image display apparatus according to claim 1, characterized in that the control means includes a scale producing means for producing a locally differently graduated scale for the region of the luminal organ on the basis of the magnitude of the variance between the pieces of radial information calculated by the correcting means, and implements control so that the produced scale and the deployed image having the distortion thereof corrected will be displayed on the display means while being juxtaposed.

6. The medical image display apparatus according to claim 1, characterized in that the control means includes a color pallet producing means for producing a color pallet to be used to locally differently color the region of the luminal organ on the basis of the magnitude of the variance between the pieces of radial information calculated by the correcting means, colors the deployed image, which has the distortion thereof corrected, according to the produced color pallet, and controls display of the colored deployed image on the display means.

7. The medical image display apparatus according to claim 1, characterized in that the control means includes an axial information calculating means for calculating axial information on the region of the luminal organ, and corrects a distortion of the deployed image on the basis of the calculated axial information and the pieces of radial information.

8. The medical image display apparatus according to claim 1, further comprising a means for selecting a rendering method for the region of the luminal organ, characterized in that: the control means produces the deployed image according to the selected rendering method.

9. The medical image display apparatus according to claim 1, wherein the correcting means corrects a distortion of the deployed image if ratio of radial information at first position in the axial direction to radial information at second position adjoined first position is out of predesignated range.

10. A medical image display method characterized in that the medical image display method comprises: a step of selectively inputting a desired medical image from among medical images taken by a medical-image radiography system; a step of reading the selectively inputted medical image from the medical-image radiography system or an external storage device, and producing a deployed image of a region of a luminal organ contained in the read medical image by tracing rays on a section which is orthogonal to a central line of the region of the luminal organ from each of the points on the central line; a step of calculating radial information of the region of the luminal organ at each position on the central line, and correcting a distortion of the deployed image so that a resolution in a circumferential direction is identical to a resolution in an axial direction, on the basis of the radial information; including obtaining a sampling pitch in the circumferential direction of the deployed image on the basis of the radical information and makes a sampling pitch in the axial direction of the deployed image the same as the sampling pitch in the circumferential direction and a step of controlling display of the corrected deployed image on a display means.

11. A medical image display program causing a computer to perform steps comprising: a step of selectively inputting a desired medical image from among medical images taken by a medical-image radiography system; a step of reading the selectively inputted medical image from the medical-image radiography system or an external storage device, and producing a deployed image of a region of a luminal organ contained in the read medical image by tracing rays on a section which is orthogonal to a central line of the region of the luminal organ from each of the points on the central line; a step of calculating radial information of the region of the luminal organ at each position on the central line, and correcting a distortion of the deployed image so that a resolution in a circumferential direction is identical to a resolution in an axial direction, on the basis of the radial information; including obtaining a sampling pitch in the circumferential direction of the deployed image on the basis of the radical information and makes a sampling pitch in the axial direction of the deployed image the same as the sampling pitch in the circumferential direction and a step of controlling display of the corrected deployed image on a display means.

* * * * *